United States Patent
Brand et al.

(10) Patent No.: US 10,946,150 B2
(45) Date of Patent: Mar. 16, 2021

(54) SYSTEM AND METHODS FOR IMPROVED COUGH SEGMENTATION

(71) Applicant: KONINKLIJKE PHILIPS N.V., Eindhoven (NL)

(72) Inventors: Maarten Leonardus Christian Brand, Murrysville, PA (US); Anandi Mahadevan, Murrysville, PA (US); James Garsteck, Scottsdale, PA (US)

(73) Assignee: Koninklijke Philips N.V., Eindhoven (NL)

( * ) Notice: Subject to any disclaimer, the term of this patent is extended or adjusted under 35 U.S.C. 154(b) by 338 days.

(21) Appl. No.: 15/571,299

(22) PCT Filed: Apr. 21, 2016

(86) PCT No.: PCT/IB2016/052252
§ 371 (c)(1),
(2) Date: Nov. 2, 2017

(87) PCT Pub. No.: WO2016/178111
PCT Pub. Date: Nov. 10, 2016

(65) Prior Publication Data
US 2018/0133418 A1    May 17, 2018

Related U.S. Application Data

(60) Provisional application No. 62/157,205, filed on May 5, 2015.

(51) Int. Cl.
*A61M 16/00* (2006.01)
*A61M 16/20* (2006.01)

(52) U.S. Cl.
CPC ...... *A61M 16/0006* (2014.02); *A61M 16/024* (2017.08); *A61M 16/202* (2014.02);
(Continued)

(58) Field of Classification Search
CPC .................................................. A61B 5/0823
(Continued)

(56) References Cited

U.S. PATENT DOCUMENTS

2013/0269698 A1*  10/2013  Balko .............. A61M 16/0051
                                                   128/204.23
2014/0007877 A1    1/2014  O'Connor
(Continued)

FOREIGN PATENT DOCUMENTS

WO    WO2012085787 A2    6/2012
WO    WO-2013118061 A1 *  8/2013  ........ A61M 16/0069
(Continued)

OTHER PUBLICATIONS

Douglas, Homnick, Mechanical Insufflation—Exsufflation for Airway Mucus Clearance. Oct. 2007. Respiratory Care vol. 52, No. 10, p. 1299. (Year: 2007).*

*Primary Examiner* — Bradley H Philips
*Assistant Examiner* — Savannah L Gabriel
(74) *Attorney, Agent, or Firm* — Daniel H. Brean

(57) ABSTRACT

Systems (100) and methods (300) for controlling coughing by subjects (106) control the opening and closing of a valve (12) (as well as partially opening and/or partially closing) to establish and disestablish a fluid communication between the airway of the subject and atmospheric pressure. The valve is opened and closed more than once during individual exhalations by the subject. Control of the valve is adjusted based on a pressure level in or near the airway of the subject.

15 Claims, 3 Drawing Sheets

(52) U.S. Cl.
CPC ... *A61M 16/201* (2014.02); *A61M 2016/0027* (2013.01); *A61M 2205/3331* (2013.01); *A61M 2230/005* (2013.01); *A61M 2230/40* (2013.01)

(58) Field of Classification Search
USPC .................................................. 128/205.18
See application file for complete search history.

(56) References Cited

U.S. PATENT DOCUMENTS

| | | |
|---|---|---|
| 2015/0231348 A1 | 8/2015 | Grace et al. |
| 2015/0320338 A1 | 11/2015 | Kane et al. |

FOREIGN PATENT DOCUMENTS

| | | |
|---|---|---|
| WO | WO2013118061 A1 | 8/2013 |
| WO | WO2015033288 A1 | 3/2015 |

\* cited by examiner

SYSTEM AND METHODS FOR IMPROVED COUGH SEGMENTATION

CROSS-REFERENCE TO RELATED APPLICATIONS

This patent application claims the priority benefit under 35 U.S.C. § 371 of international patent application no. PCT/IB2016/052252, filed Apr. 21, 2016, which claims the priority benefit under 35 U.S.C. § 119(e) of U.S. Provisional Application No. 62/157,205, filed on May 5, 2015, the contents of which are herein incorporated by reference.

BACKGROUND OF THE INVENTION

1. Field of the Invention

The present disclosure pertains to a system and method for controlling cough segmentation for patients, and, in particular, to control the opening and closing (as well as partially opening and/or partially closing) of a valve to establish and disestablish a fluid communication between the airway of the subject and atmospheric pressure.

2. Description of the Related Art

It is well-known that coughing is important in human respiratory systems. It is known that, for a variety of medical reasons, some patients cannot cough well enough to obtain the full benefits of coughing.

SUMMARY OF THE INVENTION

Accordingly, one or more aspects of the present disclosure relate to a system configured to control cough segmentation. The system comprises a cough delivery structure, one or more sensors, and one or more physical processors. The cough delivery structure is configured to fluidly communicate with an airway of a subject. The cough delivery structure includes a valve configured to selectively control, open, and close (as well as partially open and/or partially close) a fluid communication between the cough delivery structure and atmosphere. The one or more sensors are configured to generate output signals conveying information related to a pressure level within one or both of the cough delivery structure and/or the airway of the subject. The one or more physical processors are configured via computer-readable instructions to determine the pressure level based on the generated output signals; obtain a target exhalation pressure threshold; obtain one or both of a target frequency for controlling the valve and/or a target duty cycle for controlling the valve; control the valve based on one or both of the target frequency and/or the target duty cycle; compare the pressure level during a first exhalation by the subject with the target exhalation pressure threshold; adjust one or both of the target frequency and/or the target duty cycle; and control the valve based on one or both of the adjusted target frequency and/or the adjusted target duty cycle.

Yet another aspect of the present disclosure relates to a method of controlling cough segmentation. The method comprises generating output signals conveying information related to a pressure level within one or both of the cough delivery structure and/or an airway of the subject; determining the pressure level based on the generated output signals; obtaining a target exhalation pressure threshold; obtaining one or both of a target frequency for controlling the valve; controlling the valve based on one or both of the target frequency and/or the target duty cycle; comparing the pressure level during a first exhalation by the subject with the target exhalation pressure threshold; adjusting one or both of the target frequency and/or the target duty cycle in response to the pressure level during the first exhalation by the subject not reaching the target exhalation pressure threshold; and controlling the valve based on one or both of the adjusted target frequency and/or the adjusted target duty cycle.

Still another aspect of present disclosure relates to a system configured to control cough segmentation. The system comprises means for generating output signals conveying information related to a pressure level within one or both of the cough delivery structure and/or an airway of the subject; means for determining the pressure level based on the generated output signals; means for obtaining a target exhalation pressure threshold; means for obtaining one or both of a target frequency for controlling the valve; means for controlling the valve based on one or both of the target frequency and/or the target duty cycle; means for comparing the pressure level during a first exhalation by the subject with the target exhalation pressure threshold; means for adjusting one or both of the target frequency and/or the target duty cycle, the means for adjusting being operative in response to the pressure level during the first exhalation by the subject not reaching the target exhalation pressure threshold; and means for controlling the valve based on one or both of the adjusted target frequency and/or the adjusted target duty cycle.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
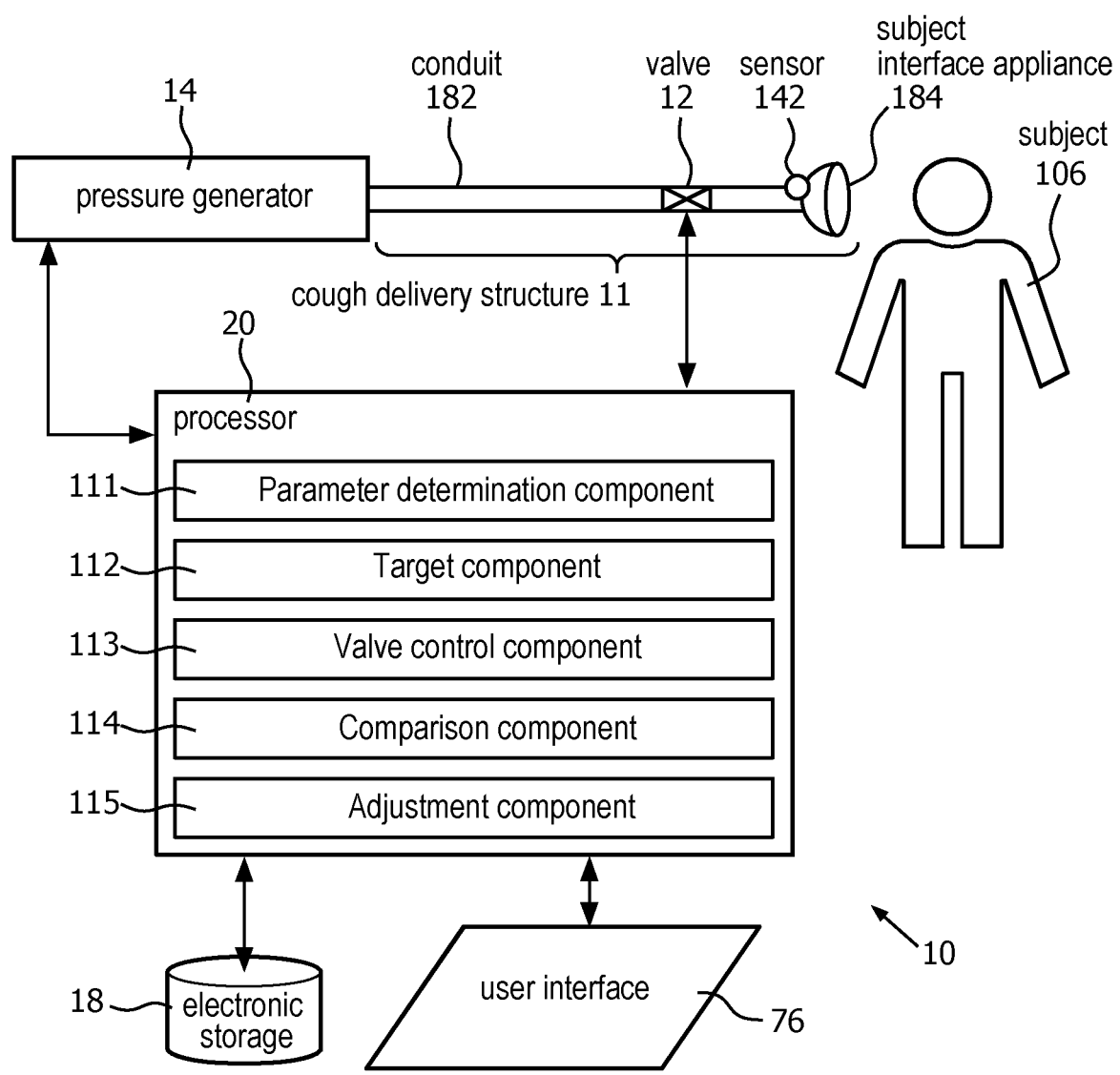
FIG. 1 schematically illustrates a system configured to control cough segmentation and/or aid coughing for a subject, in accordance with one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates a system 10 configured to control cough segmentation and/or aid coughing for a subject 106, in accordance with one or more embodiments. During typical, natural, or non-aided coughing in users who cough well enough to obtain all or most of the benefits of coughing, the pressure level in the airway may be rapidly decreased between a higher pressure level (e.g. immediately after inhalation) and a lower pressure level (e.g. immediately after exhalation). The term rapidly may refer to a cough occurring in less than 5 seconds, less than 4 seconds, less than 3 seconds, less than 2 seconds, less than 1 second, less than 0.5 seconds, and/or another suitable period. In some case, the pressure level in the airway may fluctuate between different pressure levels, for example one or more higher pressure levels and one or more lower pressure levels. Such fluctuations may occur at a frequency of about 1 Hz, about 2 Hz, about 3 Hz, about 4 Hz, about 5 Hz, about 6 Hz, about 7 Hz, about 8 Hz, about 9 Hz, about 10 Hz, and/or other suitable frequencies for the purpose of coughing. Individual fluctuations may be referred to as cough segments, and having or controlling multiple fluctuations may be referred to as cough segmentation.

In some embodiments, system 10 may be configured to control cough segmentation and/or aid coughing for subject 106 who breathes independently. In some embodiments, system 10 may be configured to control cough segmentation and/or aid coughing for subject 106 having one or more medical issues related to respiratory function and/or lung function. In some embodiments, system 10 may be configured to operate during and/or in conjunction forceful exhalation by subject 106 for one or more exhalations.

System 10 may include a cough delivery structure 11, one or more sensors 142, a pressure generator 14, one or more physical processors 20, various computer program components, electronic storage 18, a user interface structure 76, and/or other components. The computer program components may include a parameter determination component 111, a target component 112, a valve control component 113, a comparison component 114, an adjustment component 115, and/or other components.

Cough delivery structure 11 may include one or more of a subject interface appliance 184, a valve 12, a conduit 182, and/or other components. Cough delivery structure 11 may be configured and/or positioned such that subject 106 exhales into cough delivery structure 11. Conduit 182 may include a rigid or flexible length of hose, tubing, and/or other conduit, and/or combination thereof that fluidly communicated with user 106 and/or subject interface appliance 184. In embodiments that include pressure generator 14, conduit 182 may form a flow path that fluidly connects pressure generator 14 with user 106 and/or subject interface appliance 184. Conduit 182 may comprise a standard 22 mm diameter hose (other common diameters range between ¾" and 1") or, in certain embodiments, a much smaller diameter hose that is in the range of ⅓ of a standard size hose. Such a hose, which may be referred to as a restricted flow hose or limited flow hose, (for example, having a diameter ranging between ¼" and ⅜", or alternatively between 6 mm and 9 mm) may have a greater resistance to gas flow and/or may be smaller and/or less obtrusive.

Valve 12 may be configured to open and close as well as partially open and/or partially close. In some embodiments, valve 12 may be configured to open and close selectively, controllably, and/or programmatically, e.g. under control of processor 20 and/or valve control component 113. In some embodiments, valve 12 may be configured to be controlled, e.g. by valve control component 113, to varying levels of resistance, including levels corresponding to valve 12 being partially open and/or partially closed. Valve 12 may be configured to alternate between multiple levels of resistance according to a particular rate, e.g. the target frequency. In some embodiments, controlling valve 12 (as well as partially opening and/or partially closing) establishes and disestablishes flow paths from the airway of user 106. For example, in some embodiments, opening valve 12 establishes fluid communication between the airway of user 106 (or subject interface appliance 184, or one or more components of cough delivery structure 11) and the atmosphere (or a volume having either an atmospheric pressure level or a near-atmospheric pressure level, the volume being large enough to decrease the pressure level in or near the airway of user 106 within a second from more than 5 cm-$H_2O$ to less than 1 cm-$H_2O$. As used herein, the term near-atmospheric may refer to pressure levels at or below 1 cm-$H_2O$. In some embodiments, valve 12 may be an exhalation valve.

In some embodiments, valve 12 may be a one-way valve. As used in this disclosure, whenever opening and closing valve 12 is described, partially opening and/or partially closing valve 12 is intended to be included in the scope, and envisioned in some embodiments. As used in this disclosure, the term opening (a valve) may refer to any degree of increasing the flow through a valve and/or reducing the resistance to flow through a valve and/or conduit by virtue of moving at least some component of the valve. As used in this disclosure, the term closing (a valve) may refer to any degree of decreasing the flow through a valve and/or increasing the resistance to flow through a valve and/or conduit by virtue of moving at least some component of the valve.

In some embodiments, opening valve 12 may cause a reduction of a pressure level in or near the airway of subject 106 (and/or in or near cough delivery structure 11, at or near valve 12, and/or elsewhere within system 10), e.g. from a pressure level at or above a target pressure level (e.g. a target exhalation pressure threshold) to an atmospheric pressure level or a near-atmospheric pressure level. In some embodiments, closing valve 12 may cause an increase of a pressure level in or near the airway of subject 106 (and/or in or near cough delivery structure 11, at or near valve 12, and/or elsewhere within system 10), e.g. from an atmospheric pressure level or a near-atmospheric pressure level to a pressure level above an atmospheric pressure level or a near-atmospheric pressure level. For example, closing valve 12 while subject 106 is exhaling may increase the pressure level in or near the airway of subject 106 (and/or in or near cough delivery structure 11, at or near valve 12, and/or elsewhere within system 10).

The illustration of valve 12 including one member in FIG. 1 is not intended to be limiting. System 10 may include one or more valves. The illustration of a particular symbol or icon for valve 12 in FIG. 1 is exemplary and not intended to be limiting in any way. In some embodiments, valve 12 may be configured to be opened by a fraction, a percentage, a degree, a maximum flow rate, and/or any other manner that is neither fully open nor fully closed.

Pressure generator 14 of system 10 in FIG. 1 may be integrated, combined, coupled, and/or connected with a (positive) airway pressure device (PAP/CPAP/BiPAP®/etc.). In some embodiments, pressure generator 14 may be configured to aid and/or generate one or more desired pressure levels for the purpose of coughing. In some embodiments, pressure generator 14 may be configured to provide a pressurized flow of breathable gas for delivery to the airway of subject 106, e.g. via conduit 182, subject interface appliance 184, cough delivery structure 11, and/or another component of system 10. Subject 106 may initiate one or more phases of respiration. Respiratory therapy may be implemented as cough control, cough segmentation control, pressure control, pressure support, volume control, and/or other types of support and/or control. For example, to support inspiration, the pressure of the pressurized flow of breathable gas may be adjusted to an inspiratory pressure. Alternatively, and/or simultaneously, to support expiration, the pressure and/or flow of the pressurized flow of breathable gas may be adjusted to an expiratory pressure. Adjustments may be made numerous times in implementations using auto-titrating for providing respiratory support through the delivery of the pressurized flow of breathable gas.

In addition to alternating between multiple pressure, flow, or volume levels, the inhalation pressure level (and/or other levels) may ramp up or down according to a predetermined slope (absolute and/or relative, e.g. dependent on breathing rate) for any specified section of a phase. Similar features may be available for exhalation phases. The pressure levels may be either predetermined and fixed, follow a predetermined dynamic characteristic, or they may dynamically change breath-to-breath or night-to-night depending on sensed breathing, breathing disorder, or other physiological characteristics. Pressure generator 14 may be configured to adjust one or more of pressure levels, flow, humidity, velocity, acceleration, and/or other parameters of a pressurized flow of breathable gas, e.g. in substantial synchronization with the breathing cycle of the subject.

Subject interface appliance 184 of system 10 in FIG. 1 is configured to deliver the pressurized flow of breathable gas to the airway of subject 106. As such, subject interface appliance 184 may include any appliance suitable for this function. In some embodiments, pressure generator 14 is a dedicated ventilation device and subject interface appliance 184 is configured to be removably coupled with another interface appliance being used to deliver respiratory therapy to subject 106. For example, subject interface appliance 184 may be configured to engage with and/or be inserted into an endotracheal tube, a tracheotomy portal, and/or other interface appliances. In one embodiment, subject interface appliance 184 is configured to engage the airway of subject 106 without an intervening appliance. In this embodiment, subject interface appliance 184 may include one or more of an endotracheal tube, a nasal cannula, a tracheotomy tube, a nasal mask, a nasal/oral mask, a full-face mask, a total facemask, and/or other interface appliances that communicate a flow of gas with an airway of a subject. The present disclosure is not limited to these examples, and contemplates delivery of the pressurized flow of breathable gas to subject 106 using any subject interface.

One or more sensors 142 of system 10 in FIG. 1 may be configured to generate output signals conveying information related to physiological, environmental, and/or subject-specific (medical) parameters, pressure levels, and/or other information. The pressure levels may be related to the airway of subject 106, cough delivery structure 11, and/or other components of system 10. In some embodiments, the conveyed information may be related to parameters associated with the state and/or condition of subject 106, motion of subject 106, wakefulness and/or sleep state of the subject, the breathing of subject 106, the heart rate of subject 106, the respiratory rate of subject 106, vital signs of subject 106, including one or more temperatures, oxygen saturation of arterial blood ($SpO_2$), whether peripheral or central, and/or other parameters.

Sensors 142 may include one or more of a light sensor, an optical sensor, a temperature sensor, a pressure sensor, a weight sensor, an electromagnetic (EM) sensor, an infra-red (IR) sensor, a microphone, a transducer, a still-image camera, a video camera, and/or other sensors and combinations thereof.

The illustration of sensor 142 including one member in FIG. 1 is not intended to be limiting. System 10 may include one or more sensors. The illustration of a particular symbol or icon for sensor 142 in FIG. 1 is exemplary and not intended to be limiting in any way. Resulting signals or information from one or more sensors 142 may be transmitted to processor 20, user interface structure 76, electronic storage 18, and/or other components of system 10. This transmission can be wired and/or wireless.

One or more sensors 142 may be configured to generate output signals in an ongoing manner, e.g. throughout a minute, an hour, a day, a week, a month, and/or year(s). This may include generating signals intermittently, periodically (e.g. at a sampling rate), continuously, continually, at varying intervals, and/or in other ways that are ongoing during at least a portion of period of a day, week, month, or other duration. The sampling rate may be about 0.01 ms, 0.1 ms, 1 ms, 0.01 second, 0.1 second, 1 second, about 10 seconds, about 1 minute, and/or other sampling rates. It is noted that multiple individual sensors may operate using different sampling rates, as appropriate for the particular output signals and/or (frequencies related to particular) parameters derived therefrom. For example, in some embodiments, the generated output signals may be considered as a vector of output signals, such that a vector includes multiple samples of information conveyed related to one or more parameters of the subject. Different parameters may be related to different vectors. A particular parameter determined in an ongoing manner from a vector of output signals may be considered as a vector of that particular parameter.

Physical processor 20 (interchangeably referred to herein as processor 20) is configured to provide information processing and/or system control capabilities in system 10. As such, processor 20 may include one or more of a digital processor, an analog processor, a digital circuit designed to process information, an analog circuit designed to process information, and/or other mechanisms for electronically processing information. In order to provide the functionality attributed to processor 20 herein, processor 20 may execute one or more components. The one or more components may be implemented in software; hardware; firmware; some combination of software, hardware, and/or firmware; and/or otherwise implemented. Although processor 20 is shown in FIG. 1 as a single entity, this is for illustrative purposes only.

In some embodiments, processor 20 may include a plurality of processing units. These processing units may be physically located within the same device, or processor 20 may represent processing functionality of a plurality of devices operating in coordination.

As is shown in FIG. 1, processor 20 is configured to execute one or more computer program components. The one or more computer program components include one or more of parameter determination component 111, target component 112, valve control component 113, comparison component 114, adjustment component 115, and/or other components. Processor 20 may be configured to execute components 111-115 by software; hardware; firmware; some combination of software, hardware, and/or firmware; and/or other mechanisms for configuring processing capabilities on processor 20.

It should be appreciated that although components 111-115 are illustrated in FIG. 1 as being co-located within a single processing unit, in embodiments in which processor 20 includes multiple processing units, one or more of components 111-115 may be located remotely from the other components. The description of the functionality provided by the different components 111-115 described below is for illustrative purposes, and is not intended to be limiting, as any of components 111-115 may provide more or less functionality than is described. For example, one or more of components 111-115 may be eliminated, and some or all of its functionality may be provided by other ones of components 111-115. Note that processor 20 may be configured to execute one or more additional components that may perform some or all of the functionality attributed below to one of components 111-115.

As used herein, the term "determine" (and derivatives thereof) may include measure, calculate, compute, estimate, approximate, generate, and/or otherwise derive, and/or any combination thereof. As used herein, the term "obtain" (and derivatives thereof) may include active and/or passive retrieval, determination, derivation, transfer, upload, download, submission, and/or exchange of information, and/or any combination thereof.

Parameter determination component 111 may be configured to determine parameters, e.g. based on output signals generated by sensor 142. In some embodiments, parameter determination component 11 may be configured to determine a pressure level based on output signals generated by sensor 142. For example, parameter determination component 11 may be configured to determine a pressure level in or near the airway of subject 106, in or near cough delivery structure 11, at or near valve 12, and/or elsewhere within system 10.

Target component 112 may be configured to determine and/or obtain a target exhalation pressure threshold. In some embodiments, a target exhalation pressure threshold may be about 25 cm-$H_2O$, about 30 cm-$H_2O$, about 35 cm-$H_2O$, about 40 cm-$H_2O$, about 50 cm-$H_2O$, about 60 cm-$H_2O$, about 70 cm-$H_2O$, about 80 cm-$H_2O$, about 90 cm-$H_2O$, about 100 cm-$H_2O$, and/or other suitable pressure level. In some embodiments, target component 112 may be configured to determine and/or obtain a target frequency for controlling valve 12 and/or establishing and disestablishing fluid communication with subject 106. In some embodiments, target component 112 may be configured to determine and/or obtain a target frequency for opening and closing valve 12, or for controlling valve 12. For example, a target frequency may correspond to the rate of opening and closing valve 12. In some embodiments, a target frequency may be about 1 Hz, about 2 Hz, about 3 Hz, about 4 Hz, about 5 Hz, about 6 Hz, about 7 Hz, about 8 Hz, about 9 Hz, about 10 Hz, and/or other suitable frequencies for the purpose of coughing. In some embodiments, target component 112 may be configured to determine and/or obtain a target duty cycle for opening and closing valve 12. For example, a target duty cycle may reflect a first duration of opening valve 12 and/or a second duration for closing valve 12. The first and second duration may be represented by amounts of time, by percentages of the period that includes opening and closing valve 12 once, and/or in other ways that correspond hereto. For example, a target duty cycle for opening and closing may be about 50%-50%, about 60%-40%, about 40%-60%, about 70%-30%, about 30%-70%, about 80%-20%, about 20%-80%, about 90%-10%, about 10%-90%, and/or other percentages, respectively.

In some embodiments, user 106 may set, select, and/or adjust the target exhalation pressure threshold. In some embodiments, a caregiver and/or medical professional may set, select, and/or adjust the target exhalation pressure threshold, e.g. via a remote and/or networked connection to system 10. In some embodiments, system 10 may be configured to determine an adjustment of the target exhalation pressure threshold, during operation of system 10.

Valve control component 113 may be configured to control valve 12. Controlling valve 12 may include opening, closing, partially opening, and/or partially closing valve 12. In some embodiments, valve component 113 may be configured to open valve 12 by a fraction, a percentage, a degree, a maximum flow rate, and/or any other manner that is neither fully open nor fully closed. In some embodiments, valve control component 113 may be configured to control, open, and/or close valve 12 based on a target frequency. In some embodiments, valve control component 113 may be configured to control, open, and/or close valve 12 based on a target duty cycle. In some embodiments, valve control component 113 may be configured to control, open, and/or close valve 12 based on a target exhalation pressure threshold. By way of non-limiting example, valve control component 113 may be configured to control, open, and/or close valve 12 based on a target frequency of about 5 Hz and a target duty cycle of about 50%.

Comparison component 114 may be configured to compare pressure levels to pressure thresholds, including but not limited to a target exhalation pressure threshold. In some embodiments, comparison component 114 may be configured to determine whether a particular pressure level reaches, meets, and/or breaches one or more particular pressure thresholds, including but not limited to a target exhalation pressure threshold.

In some embodiments, comparison component 114 may be configured to perform multiple comparisons during a single exhalation by subject 106. Results of comparisons by comparison component 114 may be used by other computer program components, including but not limited to adjustment component 115.

Adjustment component 115 may be configured to determine and/or effectuate adjustments to the control of valve 12. In some embodiments, adjustments may be based on determinations and/or comparisons by other components, including but not limited to comparison component 114. For example, adjustments may include one or more of adjustments to a target exhalation pressure threshold, adjustments to a target frequency, adjustments to a target duty cycle, and/or any combinations thereof, as well as other adjustments to the operation of system 10. In some embodiments, adjustments may be made during the same exhalation by subject 106 as was used for a determination and/or comparison by other components, including but not limited to comparison component 114. In some embodiments, operations of comparison component 114 may pertain to a first exhalation, and operations of adjustment component 115 may pertain to a second exhalation that is subsequent to the first exhalation.

In some embodiments, adjustment component 115 may be configured to determine and/or effectuate adjustments to the control of valve 12 in response to a particular pressure level not reaching the target exhalation pressure threshold. For example, the particular pressure level may be in or near the airway of subject 106, in or near cough delivery structure 11, at or near valve 12, and/or elsewhere within system 10. In some embodiments, the particular pressure level may be based on a combination of one or more pressure levels in or near the airway of subject 106, in or near cough delivery structure 11, at or near valve 12, and/or elsewhere within system 10. For example, adjustments may include a reduction of the target frequency for opening and closing valve 12, controlling valve 12, and/or establishing the fluid communication by opening valve 12. For example, adjustments may include an adjustment of the target duty cycle such that the duration of valve 12 being open is reduced and/or the duration of valve 12 being closed is increased.

In some embodiments, valve control component 113 may be configured to control, open, and/or close valve 12 based on one or more adjustments as determined and/or effectuate by adjustment component 15.

Figure 2:
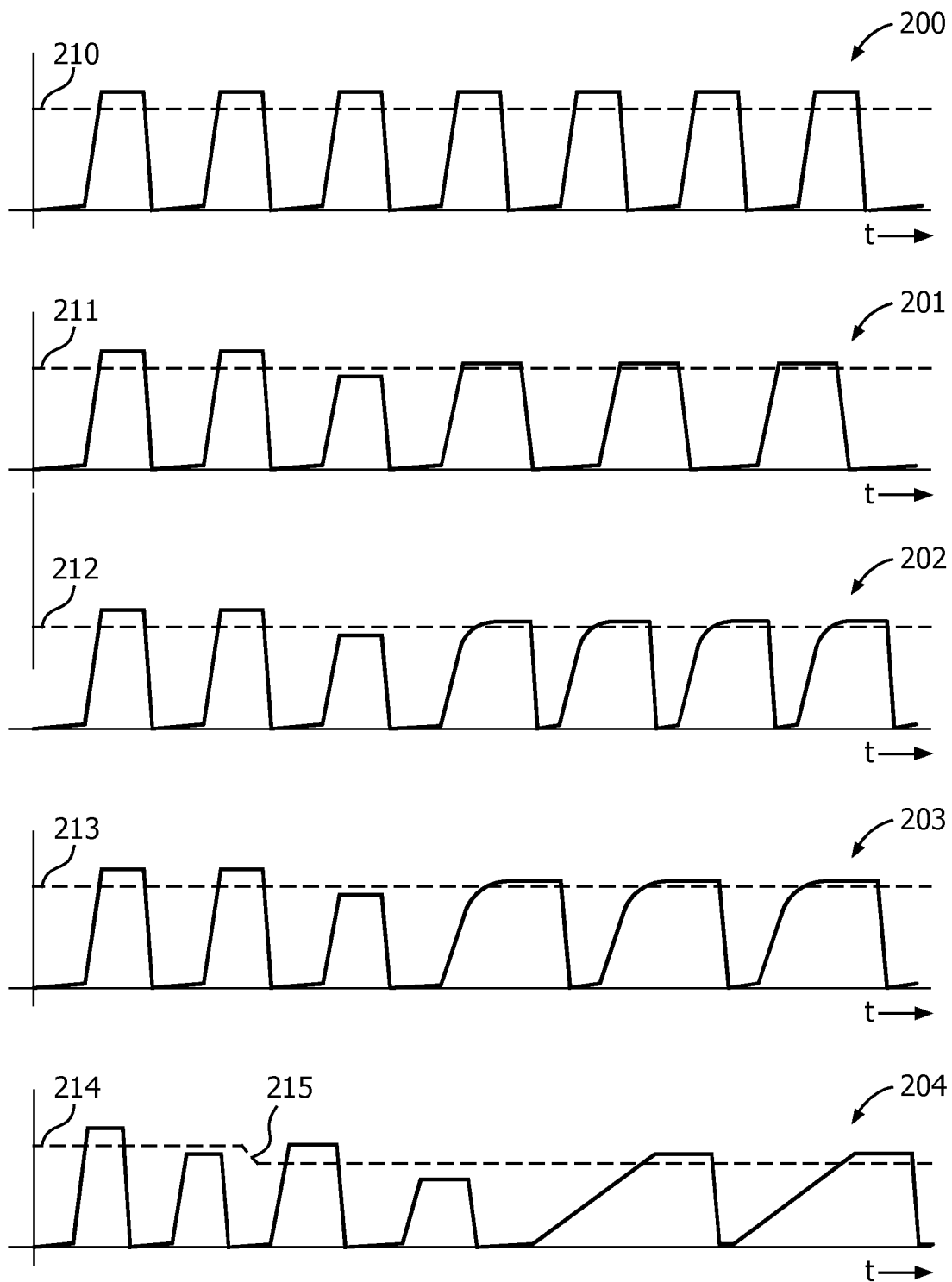
FIG. 2 illustrates graphs representing pressure levels during the use of different embodiments of a system configured to control cough segmentation and/or aid coughing for a subject.

By way of illustration, FIG. 2 illustrates graphs 200-201-202-203-204 representing pressure levels during the use of different embodiments and/or different scenarios for the operation of system 10. In graph 200, level 210 indicates a target exhalation pressure threshold. In graph 201, level 211 indicates a target exhalation pressure threshold. In graph 202, level 212 indicates a target exhalation pressure threshold. In graph 203, level 213 indicates a target exhalation pressure threshold. In graph 204, level 214 indicates a target exhalation pressure threshold.

For example, the pressure level in graph 200 represents a subject coughing by virtue of a cough delivery structure such as cough delivery structure 11 (shown in FIG. 1) at a particular frequency (e.g. 5 Hz) and duty cycle (e.g. 50%) for a particular number of cough segments (as shown here, seven cough segments). As indicated in graph 200, the pressure level reaches level 210 repeatedly, for consecutive cough segments. Accordingly, the particular frequency and the particular duty cycle may not need to be adjusted as described elsewhere in this disclosure.

For example, the pressure level in graph 201 represents a subject coughing by virtue of a cough delivery structure such as cough delivery structure 11 (shown in FIG. 1) at a particular frequency (e.g. 5 Hz) and duty cycle (e.g. 50%) for a particular number of cough segments for which the pressure level reaches level 211 (as shown here, the pressure level reaches level 211 for two cough segments). The pressure level fails to reach level 211 for the third cough segment. As indicated in graph 201, the particular frequency is reduced (e.g. to 4 Hz) such that more time is available for the pressure level to reach level 211. As shown in graph 201, the pressure level reaches level 211 for the fourth, fifth, and sixth cough segments. Note that the duty cycle has not been adjusted in the example illustrated by graph 201.

For example, the pressure level in graph 202 represents a subject coughing by virtue of a cough delivery structure such as cough delivery structure 11 (shown in FIG. 1) at a particular frequency (e.g. 5 Hz) and duty cycle (e.g. 50%) for a particular number of cough segments for which the pressure level reaches level 212 (as shown here, the pressure level reaches level 212 for two cough segments). The pressure level fails to reach level 212 for the third cough segment. As indicated in graph 202, the particular duty cycle is altered such that the valve (e.g. valve 12 as shown in FIG. 1) is closed for more than 50% of each cycle of opening and closing the valve (e.g. to 70%) such that more time is available for the pressure level to reach level 212. As shown in graph 202, the pressure level reaches level 212 for the fourth, fifth, sixth and seventh cough segments. Note that the frequency has not been adjusted in the example illustrated by graph 202.

For example, the pressure level in graph 203 represents a subject coughing by virtue of a cough delivery structure such as cough delivery structure 11 (shown in FIG. 1) at a particular frequency (e.g. 5 Hz) and duty cycle (e.g. 50%) for a particular number of cough segments for which the pressure level reaches level 213 (as shown here, the pressure level reaches level 213 for two cough segments). The pressure level fails to reach level 213 for the third cough segment. As indicated in graph 203, the particular duty cycle is altered such that the valve (e.g. valve 12 as shown in FIG. 1) is closed for more than 50% of each cycle of opening and closing the valve (e.g. to 75%) such that more time is available for the pressure level to reach level 213. As indicated in graph 203, the particular frequency is reduced (e.g. to 4 Hz) such that more time is available for the pressure level to reach level 213. As shown in graph 203, the pressure level reaches level 212 for the fourth, fifth, and sixth cough segments. Note that both the frequency and the duty cycle have been adjusted in this example.

For example, the pressure level in graph 204 represents a subject coughing by virtue of a cough delivery structure such as cough delivery structure 11 (shown in FIG. 1) at a particular frequency (e.g. 5 Hz) and duty cycle (e.g. 50%) for a particular number of cough segments for which the pressure level reaches level 214 (as shown here, the pressure level reaches level 214 for one cough segment). The pressure level fails to reach level 214 for the second cough segment. As indicated in graph 204, level 214 is lowered at point 215 and the particular frequency is reduced (e.g. to 4 Hz) such that more time is available for the pressure level to reach adjusted level 214. As shown in graph 204, the pressure level reaches adjusted level 214 for the third cough segment, but not for the fourth cough segment. In response to the pressure level not reaching adjusted level 214, both the particular frequency and the duty cycle are adjusted, such that more time is available for the pressure level to reach adjusted level 214. As shown in graph 204, the pressure level reaches adjusted level 214 for the fifth and sixth cough segments. Note that both the frequency and the duty cycle have been adjusted in this example.

Referring to FIG. 1, in some embodiments, system 10 may be configured to first adjust the duty cycle in an attempt to reach a target exhalation pressure threshold, and subsequently adjust the target frequency. In some embodiments, system 10 may be configured to first adjust the target frequency in an attempt to reach a target exhalation pressure threshold, and subsequently adjust the duty cycle.

In some embodiments, system 10 may be configured to control valve 12 based on comparisons between the pressure level (e.g. in or near the airway of subject 106, in or near cough delivery structure 11, at or near valve 12, and/or elsewhere within system 10) and a target exhalation pressure threshold, during one or more exhalations by subject 106. For example, in response to the pressure level the target exhalation pressure threshold, system 10 may be configured to open valve 12 (for a predetermined amount of time and/or until a particular pressure level has been reached, such as an atmospheric pressure level). In response to the predetermined amount of time passing and/or the particular pressure level having been reached, system 10 may be configured to close valve 12. This process of opening and closing valve 12 may be repeated until one or more exhalations have been completed.

User interface structure 76 is configured to provide an interface between system 10 and a user through which the user can provide and/or receive information. This enables data, results, and/or instructions and any other communicable items, collectively referred to as "information," to be communicated between the user and system 10. Examples of interface devices suitable for inclusion in user interface structure 76 include a keypad, buttons, switches, a keyboard, knobs, levers, a display screen, a touch screen, speakers, a microphone, an indicator light, an audible alarm, and a printer. Information may be provided to the subject by user interface structure 76 in the form of auditory signals, visual signals, tactile signals, and/or other sensory signals.

By way of non-limiting example, user interface structure 76 may include a light source capable of emitting light. The light source may include, for example, one or more of at least one LED, at least one light bulb, a display screen, and/or other sources. User interface structure 76 may control the light source to emit light in a manner that conveys to the subject information related to operation of system 10. Note that subject 106 and the user of system 10 may be one and the same person.

It is to be understood that other communication techniques, either hard-wired or wireless, are also contemplated herein as user interface structure 76. For example, in one embodiment, user interface structure 76 may be integrated with a removable storage interface provided by electronic storage 18. In this example, information is loaded into system 10 from removable storage (e.g., a smart card, a flash drive, a removable disk, etc.) that enables the user(s) to customize the implementation of system 10. Other exemplary input devices and techniques adapted for use with system 10 as user interface structure 76 include, but are not limited to, an RS-232 port, RF link, an IR link, modem (telephone, cable, Ethernet, internet or other). In short, any technique for communicating information with system 10 is contemplated as user interface structure 76.

Electronic storage 18 of system 10 in FIG. 1 comprises physical electronic storage media that electronically stores information, e.g. digital information. The electronic storage media of electronic storage 18 may include one or both of system storage that is provided integrally (i.e., substantially non-removable) with system 10 and/or removable storage that is removably connectable to system 10 via, for example, a port (e.g., a USB port, a FireWire port, etc.) or a drive (e.g., a disk drive, etc.). Electronic storage 18 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), network-attached storage (NAS), and/or other electronically readable storage media. Electronic storage 18 may include virtual storage resources, such as storage resources provided via a cloud and/or a virtual private network. Electronic storage 18 may store software algorithms, information determined by processor 20, information received via user interface 76, and/or other information that enables system 10 to function properly. For example, electronic storage 18 may record or store a target frequency, target duty cycle, and/or other parameters (as discussed elsewhere herein), and/or other information. Electronic storage 18 may be a separate component within system 10, or electronic storage 18 may be provided integrally with one or more other components of system 10 (e.g., processor 20).

Figure 3:
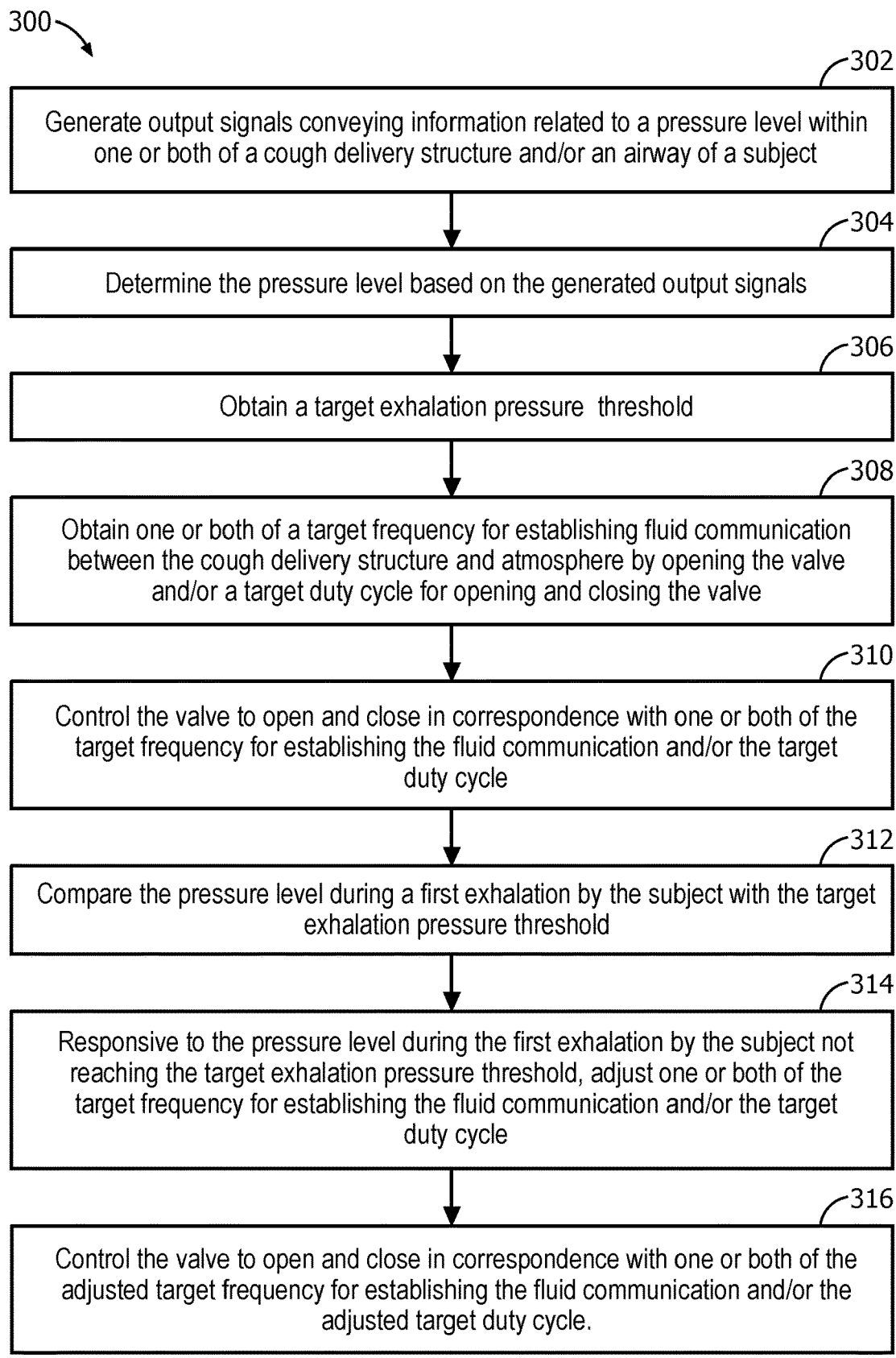
FIG. 3 illustrates a method to control cough segmentation and/or aid coughing for a subject, according to one or more embodiments.

FIG. 3 illustrates a method 300 for controlling cough segmentation. The operations of method 300 presented below are intended to be illustrative. In some embodiments, method 300 may be accomplished with one or more additional operations not described, and/or without one or more of the operations discussed. Additionally, the order in which the operations of method 300 are illustrated in FIG. 3 and described below is not intended to be limiting.

In some embodiments, method 300 may be implemented in one or more processing devices (e.g., a digital processor, an analog processor, a digital circuit designed to process information, an analog circuit designed to process information, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, output signals are generated that convey information related to a pressure level within one or both of the cough delivery structure and/or an airway of the subject. In some embodiments, operation 302 is performed by a sensor the same as or similar to sensor 142 (shown in FIG. 1 and described herein).

At an operation 304, the pressure level is determined based on the generated output signals. In some embodiments, operation 304 is performed by a parameter determination component the same as or similar to parameter determination component 111 (shown in FIG. 1 and described herein).

At an operation 306, a target exhalation pressure threshold is obtained. In some embodiments, operation 306 is performed by a target component the same as or similar to target component 112 (shown in FIG. 1 and described herein).

At an operation 308, one or both of a target frequency and/or a target duty cycle is obtained. The target frequency is for establishing fluid communication between the cough delivery structure and atmosphere by opening the valve. The target duty cycle is for opening and closing the valve. In some embodiments, operation 308 is performed by a target component the same as or similar to target component 112 (shown in FIG. 1 and described herein).

At an operation 310, the valve is controlled to open and close based on one or both of the target frequency for establishing the fluid communication and/or the target duty cycle. In some embodiments, operation 310 is performed by a valve control component the same as or similar to valve control component 113 (shown in FIG. 1 and described herein).

At an operation 312, the pressure level during a first exhalation by the subject is compared with the target exhalation pressure threshold. In some embodiments, operation 312 is performed by a comparison component the same as or similar to comparison component 114 (shown in FIG. 1 and described herein).

At an operation 314, in response to the pressure level during the first exhalation by the subject not reaching the target exhalation pressure threshold, one or both of the target frequency for establishing the fluid communication and/or the target duty cycle is adjusted. In some embodiments, operation 314 is performed by a adjustment component the same as or similar to adjustment component 115 (shown in FIG. 1 and described herein).

At an operation 316, the valve is controlled to open and close based on one or both of the adjusted target frequency for establishing the fluid communication and/or the adjusted target duty cycle. In some embodiments, operation 316 is performed by a valve control component the same as or similar to valve control component 113 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to control cough segmentation, the system comprising:
    a cough delivery structure configured to fluidly communicate with an airway of a subject, wherein the cough delivery structure includes a valve configured to selectively control a fluid communication between the cough delivery structure and atmosphere;
    one or more sensors configured to generate output signals conveying information related to a pressure level within one or both of the cough delivery structure and the airway of the subject; and
    one or more physical processors configured via computer-readable instructions to:
        obtain a target exhalation pressure threshold;
        obtain, for controlling the valve,
            a target frequency that corresponds to a rate of opening and closing the valve and
            a target duty cycle that reflects percentages of a first duration of opening the valve and a second duration of closing the valve;
        control the valve to open and close based on the target frequency and the target duty cycle to cause multiple consecutive cough segments;
        determine the pressure level during the multiple consecutive cough segments based on the generated output signals;
        compare the pressure level during a first exhalation of the multiple consecutive cough segments to the target exhalation pressure threshold; and, responsive to the pressure level not reaching the target exhalation pressure threshold at a peak of an individual one of the multiple consecutive cough segments;
        separately performing operations of both reducing the target frequency and altering a percentage of the target duty cycle such that the pressure level breaches the target exhalation pressure threshold for remaining cough segments; and
        control the valve based on the adjustment.

2. The system of claim 1, wherein the one or more physical processors are configured to control the valve based on the adjustment during an exhalation by the subject such that the valve is opened more than once and closed more than once during the exhalation.

3. The system of claim 1, wherein adjustment of the target duty cycle includes a reduction of the first duration of opening the valve.

4. The system of claim 1, wherein the target exhalation pressure threshold is at least 25 cm-$H_2O$.

5. The system of claim 1, wherein the one or more physical processors are configured to, responsive to the pressure level not reaching the target exhalation pressure threshold during an individual one of the multiple consecutive cough segments:
    adjust the target duty cycle;
    compare the pressure level during cough segments subsequent to adjustment of the target duty cycle to the target exhalation pressure threshold, and, responsive to the pressure level during the subsequent cough segment not reaching the target exhalation pressure threshold;
    adjust the target frequency such that the pressure level breaches the target exhalation pressure threshold for the remaining cough segments.

6. A method of controlling cough segmentation, the method being implemented in a system that includes a cough delivery structure including a valve, the method comprising:
    generating output signals conveying information related to a pressure level within one or both of the cough delivery structure and an airway of the subject;
    obtaining a target exhalation pressure threshold;
    obtaining, for controlling the valve,
        a target frequency that corresponds to a rate of opening and closing the valve and
        a target duty cycle that reflects percentages of a first duration of opening the valve and a second duration of closing the valve;
    controlling the valve to open and close based on the target frequency and the target duty cycle to cause multiple consecutive cough segments;
    determining the pressure level during the multiple consecutive cough segments;
    comparing the pressure level during a first exhalation of the multiple consecutive cough segments to the target exhalation pressure threshold, and, responsive to the pressure level not reaching the target exhalation pressure threshold at a peak of an individual one of the multiple consecutive cough segments;
    adjusting operation of the valve by separately performing operations of both reducing the target frequency and altering a percentage of the target duty cycle such that the pressure level breaches the target exhalation pressure threshold for remaining cough segments; and
    controlling the valve based on the adjustment.

7. The method of claim 6, wherein controlling the valve based on the adjustment is performed during an exhalation by the subject such that the valve is opened more than once and closed more than once during the exhalation.

8. The method of claim 6, wherein adjusting the target duty cycle includes reducing the first duration of opening the valve.

9. The method of claim 6, wherein the target exhalation pressure threshold is at least 25 cm-H$_2$O.

10. The method of claim 6, further comprising, responsive to pressure level not reaching the target exhalation pressure threshold during an individual one of the multiple consecutive cough segments:
adjusting the target duty cycle;
comparing the pressure level with the target exhalation pressure threshold subsequent to adjusting the target duty cycle; and, responsive to the pressure level during subsequent cough segments not reaching the target exhalation pressure threshold;
adjusting the target frequency such that the pressure level breaches the target exhalation pressure threshold for the remaining cough segments.

11. A system configured to control cough segmentation, the system comprising:
means for generating output signals conveying information related to a pressure level within one or both of a cough delivery structure and an airway of a subject;
means for obtaining a target exhalation pressure threshold;
means for obtaining, for controlling the valve,
a target frequency that corresponds to a rate of opening and closing the valve and
a target duty cycle that reflects percentages of a first duration of opening the valve and a second duration of closing the valve;
means for controlling the valve to open and close based on the target frequency and the target duty cycle to cause multiple consecutive cough segments;
means for determining, the pressure level during the multiple consecutive cough segments based on the generated output signals;
means for comparing the pressure level during a first exhalation of the multiple consecutive cough segments to the target exhalation pressure threshold;
means for adjusting operation of the valve by separately performing operations of both reducing the target frequency and altering a percentage of the target duty cycle such that the pressure level breaches the target exhalation pressure threshold for remaining cough segments, the means for adjusting being operative responsive to the pressure level at a peak of an individual one of the multiple consecutive cough segments not reaching the target exhalation pressure threshold; and
means for controlling the valve based on the adjustment.

12. The system of claim 11, wherein the means for controlling the valve is configured to control the valve to open and close more than once during an exhalation.

13. The system of claim 11, wherein adjusting the target duty cycle includes reducing the first duration of opening the valve.

14. The system of claim 11, wherein the target exhalation pressure threshold is at least 25 cm-H$_2$O.

15. The system of claim 11, wherein the system is configured to, responsive to the pressure level not reaching the target exhalation pressure threshold during an individual one of the multiple consecutive cough segments:
adjust the target duty cycle;
compare the pressure level with the target exhalation pressure threshold subsequent to adjusting the target duty cycle; and, responsive to the pressure level during subsequent cough segments not reaching the target exhalation pressure threshold;
adjust the target frequency such that the pressure level breaches the target exhalation pressure threshold for the remaining cough segments.

* * * * *